(12) United States Patent
Caillat et al.

(10) Patent No.: US 6,255,677 B1
(45) Date of Patent: Jul. 3, 2001

(54) CHIP-BASED ANALYSIS DEVICE COMPRISING ELECTRODES WITH LOCALIZED HEATING

(75) Inventors: Patrice Caillat, Echirolles; Philippe Peltie, Saint-Paul de Varces; Thierry Livache, Haute—Jarrie, all of (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 09/111,773

(22) Filed: Jul. 8, 1998

(30) Foreign Application Priority Data

Jul. 11, 1997 (FR) .................................................. 97 08864

(51) Int. Cl.⁷ .................................................. H01L 27/14
(52) U.S. Cl. .......................... 257/252; 257/253; 257/414; 257/467; 257/469; 257/470; 438/49
(58) Field of Search .................................... 257/252, 253, 257/414, 467, 469, 470; 438/49

(56) References Cited

U.S. PATENT DOCUMENTS 4,001,046 * 1/1977 Weiss et al. ......................... 136/205

5,632,957 * 5/1997 Heller et al. ......................... 422/68.1
5,777,372 * 7/1998 Kobashi ............................... 257/414
5,786,608 * 7/1998 Lescourzeres ...................... 257/253

FOREIGN PATENT DOCUMENTS

| 0 640 828 | 8/1994 | (EP) . |
| 0 724 153 | 7/1995 | (EP) . |
| 96 07917 | 9/1995 | (WO) . |
| 96 28538 | 3/1996 | (WO) . |

* cited by examiner

*Primary Examiner*—Eddie Lee
*Assistant Examiner*—Matthew E. Warren
(74) *Attorney, Agent, or Firm*—Burns Doane Swecker & Mathis (57) ABSTRACT

The invention concerns an analysis device including at least one chip (110) equipped with a plurality of analysis electrodes (112). In accordance with the invention, the device also includes means of individual heating (150) of the analysis electrodes.

The invention can be used for the analysis of chemical or biological products, for example in an antigen/antibody recognition or DNA/DNA analysis.

7 Claims, 6 Drawing Sheets

CHIP-BASED ANALYSIS DEVICE COMPRISING ELECTRODES WITH LOCALIZED HEATING

TECHNICAL FIELD

The present invention relates to an analysis device comprising an electronic chip equipped with a plurality of electrodes. Such a chip is used to constitute a miniaturized chemical or biological analysis cell. This is because each electrode of the chip can be coated individually with a compound or a material sensitive to a specific chemical or biological product.

An analysis device in accordance with the invention can be used, for example, as a glucose measurer, or as a device for blood analysis or for analysis of various chemical or biological products.

A particular application of the device of the invention in the field of molecular biology is that of antibody/antigen recognition. Similarly, the device can also be used in DNA chips.

PRIOR ART

An electronic chip for an analysis device as mentioned above may include several hundred electrodes each carrying a DNA probe. DNA probe means DNA molecules having a predetermined known sequence. The selective hybridization of DNA molecules in a medium to be analyzed with the probe molecules fixed on the electrodes makes it possible to know the composition of this medium. By way of example, it is possible to perform a genetic analysis on mutations responsible for a given type of cancer.

Of course, in other analysis applications, the probe molecules are replaced by any appropriate reagent sensitive to a given substance liable to be in the medium to be analyzed.

The accompanying FIGS. 1 to 4 illustrate the structure and use of chips with electrodes for analyzing a medium.

Figure 1:
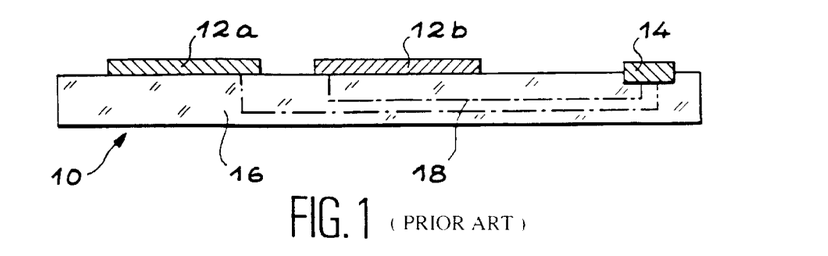
FIG. 1, already described, is a schematic section of a biological sensor chip.

FIG. 1 shows in section and schematically a biological sensor chip 10 as used for antibody/antigen recognition or as a DNA/DNA probe for a patient.

Chip 10 includes so-called analysis electrodes 12a and 12b and addressing electrodes 14. Although the number of electrodes present on an analysis chip is generally high, of the order of ten to several hundred, chip 10 of FIG. 1 is shown with only two analysis electrodes and a single addressing electrode, for obvious reasons of clarity. The analysis electrodes can be electrically addressed by corresponding addressing electrodes. However, when the number of analysis electrodes is very large, the chip may include a multiplexed addressing device making it possible to address all the analysis electrodes from a reduced number of addressing electrodes.

Addressing means making the electrical connection of one or more analysis electrodes with one or more so-called addressing electrodes generally arranged at the periphery of the chip. The addressing electrodes make it possible to apply or measure a voltage on the analysis electrodes, by means of suitable external apparatus.

Generally, analysis electrodes 12a and 12b are made of a metal such as, for example, gold or platinum. They are mutually isolated from one another on a wafer of substrate 16. Electrical connections between analysis electrodes 12a, 12b and the addressing electrodes are arranged in substrate 16 and are indicated very schematically with reference 18.

A chip, such as depicted in FIG. 1, must be configured for a particular use and the analysis electrodes are to that end made functional by coating them with probe molecules or by covering their surfaces with a deposit of appropriate reagent.

The deposition of reactive products or the transplanting of probe molecules onto the electrodes is carried out, in general, by electrodeposition.

The reagents or probe molecules deposited on the electrodes allow, as indicated previously, a selective pairing with specific molecules of a substance to be analyzed. These molecules are designated "target molecules" in the remainder of the text.

Figure 2:
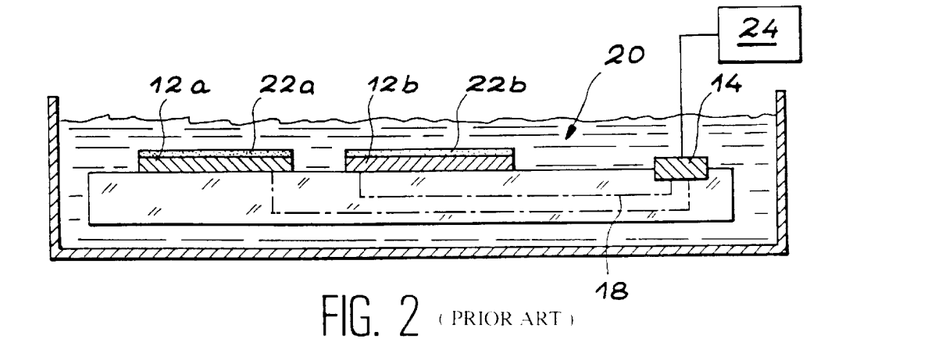
FIG. 2, already described, is a schematic section of the chip of FIG. 1 immersed in a bath of electrolyte, FIG. 3, already described, is a schematic section of the chip of FIG. 1, immersed in a bath of analyte, FIG. 4, already described, is a schematic section of the chip of FIG. 1, subjected to an analysis by fluorescence.

FIG. 2 shows chip 10 immersed in a bath of electrolyte 20. Bath of electrolyte means a bath suitable for depositing, by electrochemistry, a reagent on the electrodes, or a bath in which probe molecules which have to be fixed by electrodeposition on the electrodes are diluted.

The selective application of a bias voltage between selected analysis electrodes and a reference electrode makes it possible to fix thereon the reactive product or the probe molecules. The voltage is applied to the electrodes by means of an external generator 24 connected to addressing electrodes 14.

The probe molecules are fixed on the analysis electrodes, for example, by means of conductive polymers of polypyrrole or polyaniline type which are carriers of probe molecules.

The chip may undergo several electrochemical deposition steps, being dipped in different baths. Thus, different electrodes of the chip can be covered with different reagents, or probe molecules, sensitive to different compounds of the substances to be analyzed.

In FIG. 2, it is considered that the two electrodes 12a and 12b are respectively (and successively) covered with different reagents, or probe molecules, 22a, 22b.

At the end of the coating of the electrodes with the reagents, of probe molecules, the chip is ready to be used in order to analyze a substance, designated analyte in the remainder of the description.

Figure 3:
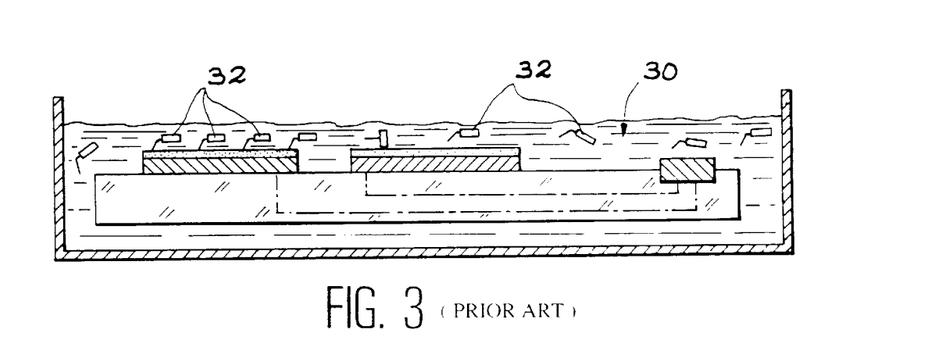

As shown in FIG. 3, chip 10 is disconnected from the generator and is immersed in a bath 30 containing the analyte.

This bath contains, for example, target molecules 32 which pair or react with the reagent or the probe molecules 22a previously deposited on the first electrode 12a. For reasons of clarity, target molecules 32 are depicted schematically and magnified.

Target molecules 32 do not however interact with the second electrode 12b, whose reactive coating, or probe molecules, are not compatible.

After having been extracted from the bath of analyte 30, the chip is analyzed in order to determine the electrodes for which a reaction or a pairing has taken place.

Figure 4:
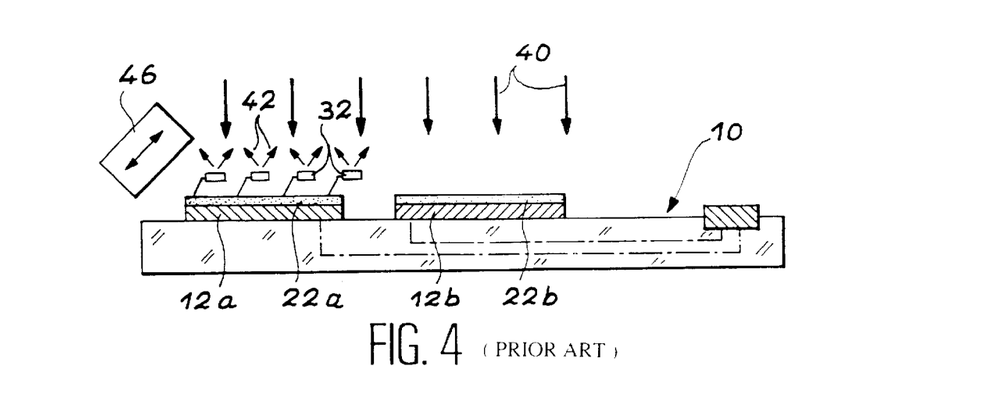

In the example described in FIG. 4, chip 10 is analyzed by a method of detection by fluorescence. Such a method is particularly suitable when target molecules 32 are marked with a fluorescent marking product referred to as a fluorophore.

However, other analysis methods such as methods of electrical measurement by impedometry, of measurement by microbalance, optical measurements by change in refractive index, and methods of analysis by radioactive marking can also be envisaged.

As shown in FIG. 4, the whole of the chip 10 is subjected to light radiation 40 of a first wavelength and coming from a light source, not depicted.

The marked target molecules absorb the light radiation 40 and emit a light radiation 42 with a characteristic second wavelength, different from the first wavelength.

A detection device 46, sensitive to the second wavelength, makes it possible to detect the light re-emitted from the electrodes carrying the target molecules marked with the fluorescent product. It is thus possible, by knowing the nature of the reagents or of the probe molecules previously deposited on each electrode, to determine the components of the analyte which are fixed thereto.

It emerges from the preceding description that a crucial step for the analysis is the so-called pairing or hybridization step during which the target molecules are fixed on the probe molecules or on the reagent.

In order to guarantee the reliability and reproducibility of the pairing or hybridization for electrodes having the same probe molecules, the chip and the analyte should in a certain number of cases be heated and maintained at a controlled constant temperature during the pairing or hybridization.

However, heating at a suitable temperature is possible only for chips on which substantially all the electrodes are coated with the same probe molecules. In fact, when different reagents or different probe molecules disposed on electrodes of one and the same chip require different hybridization or pairing temperatures, a reliable analysis is no longer possible.

A similar problem arises for the analysis chips used as DNA/DNA probes. On such a chip, a probe molecule of DNA, properly identified, is fixed on each electrode.

A plurality of distinct probe molecules can thus coat the electrodes of the chip. Each probe molecule consists of a sequence of bases, generally identified with the letters A, T, C and G, in a specific order.

When the chip is brought into contact with the analyte, a strand of DNA contained in the analyte can pair with a given probe molecule when it has a sequence of bases complementary to a sequence of bases of the probe molecule. The links possible between the bases are of two types: the A—T hydrogen bonds (bonds involving two atoms of hydrogen) and the C—G hydrogen bonds (bonds involving three atoms of hydrogen).

The pairing reaction, that is to say the links between complementary bases, is reversible. By heating the DNA strands to a temperature generally between 30° C. and 60° C., it is possible to break the hydrogen bonds.

Also, as there are two possible types of link, indicated above, which are not exactly identical, it is possible to selectively break the links of one type and not the links of the other type.

This property is particularly important for removing accidental pairings not corresponding to a complete sequence of complementary bases.

By way of example, when a probe DNA molecule consists of a sequence of 8 given bases, any strand of DNA of the analysis comprising a complete or partial complementary sequence of the 8 bases can pair at least in part with the probe molecule. By heating the paired structure of the DNA strand to an appropriate temperature, it is possible to selectively eliminate the accidental incomplete pairings and save only the pairings corresponding to the complete complementary sequence of the probe molecule of DNA.

In this case again, it is not possible to heat the chip to a temperature which is suitable for all the electrodes if these are coated with probe DNA molecules having different sequences. This is because the temperature required to break the links of a paired structure depends essentially on the first base in the sequence of the probe molecule.

DESCRIPTION OF THE INVENTION

The aim of the present invention is to provide an analysis device making it possible to perform heating to a desired temperature for each electrode of a chip, in order to perform reliable and reproducible analyses with chips comprising a large number of electrodes coated with different reagents or probe molecules.

One aim of the invention is also to provide an electronic chip-based analysis device making it possible to precisely control the temperature in the vicinity of each electrode of the chip.

One aim of the invention is also to provide a chip-based analysis device which is economic and can be used in particular for genetic analysis.

In order to achieve these aims, the object of the invention is more precisely an analysis device which includes at least one chip equipped with a plurality of analysis electrodes, and which also includes means of individual heating of the analysis electrodes.

By virtue of the means of individual heating of the analysis electrodes, it is possible, for example, to selectively heat a selected set of analysis electrodes amongst the plurality of analysis electrodes.

It is also possible, by virtue of the individual heating, to bring each electrode to a temperature specific to it.

Thus, in the case of a chip comprising electrodes coated with probe molecules of DNA, it is possible to heat each electrode to a temperature depending, for example, on the DNA sequence of the probe molecules with which it is coated.

According to a first embodiment of the device of the invention, the heating means may consist, for each electrode, of a conductive heating track disposed in the vicinity of the said electrode.

It is considered that the conductive heating track is disposed in the vicinity of an analysis electrode when the mean distance separating the conductive track from this electrode is less than the distance separating the conductive track from the other analysis electrodes of the chip.

In particular, each conductive heating track can be disposed so as to surround the electrode.

According to a variant, in which the electrodes are themselves configured in the form of conductive tracks, a conductive heating track can be respectively associated with at least one conductive track forming an electrode and then extending parallel to it.

The individual heating means may have electronic addressing circuits connected to addressing electrodes, and designed to selectively, in each conductive heating track, cause a current to flow corresponding to the desired local heating.

The supplying of current to the conductive heating tracks can be direct, using a number of addressing electrodes and circuits corresponding to the number of conductive heating tracks. The supplying of current can also take place by means of multiplexed circuits.

According to another particular embodiment of the device of the invention, in which the chip includes conductive tracks forming analysis electrodes, the heating means can include at least one electronic addressing circuit for selectively and individually applying a heating current to the conductive tracks forming analysis electrodes. Thus, the tracks have a dual function of analysis and heating electrode.

Such a measure makes it possible to reduce the size and cost of the heating means.

According to an advantageous aspect of the invention, the analysis device of the invention may also include means of mutual thermal isolation of the electrodes and the conductive heating tracks.

Mutual thermal isolation of the electrodes means isolation making it possible to reduce the thermal exchanges between neighbouring electrodes and between a given electrode and a conductive heating track associated with a neighbouring electrode of the said given electrode.

The thermal isolation means may in particular consist of an electrically isolating layer of polymer material disposed on the chip, and on which the analysis electrodes are formed. This layer of polymer material is preferably chosen with a thermal conductivity less than that of the chip.

According to a variant embodiment of the invention, the means of individual heating of the analysis electrodes may also include at least one laser source and at least one network of microlenses in order to make heating radiation converge towards selected analysis electrodes of the said plurality of analysis electrodes.

In order to perform selective and apportioned heating for each analysis electrode, the network of microlenses may be provided with a mask having regions of variable density and disposed in front of the microlenses.

In particular, the network of microlenses may be equipped with a mask having transparent regions and opaque regions. The mask may also include regions allowing the light from the laser to pass to a greater or lesser degree.

Other characteristics and advantages of the invention will emerge more clearly from the description which follows, with reference to the figures in the accompanying drawings. This description is given on a purely illustrative and non-limitative basis.

DETAILED DESCRIPTION OF EMBODIMENTS OF THE INVENTION

Figure 5:
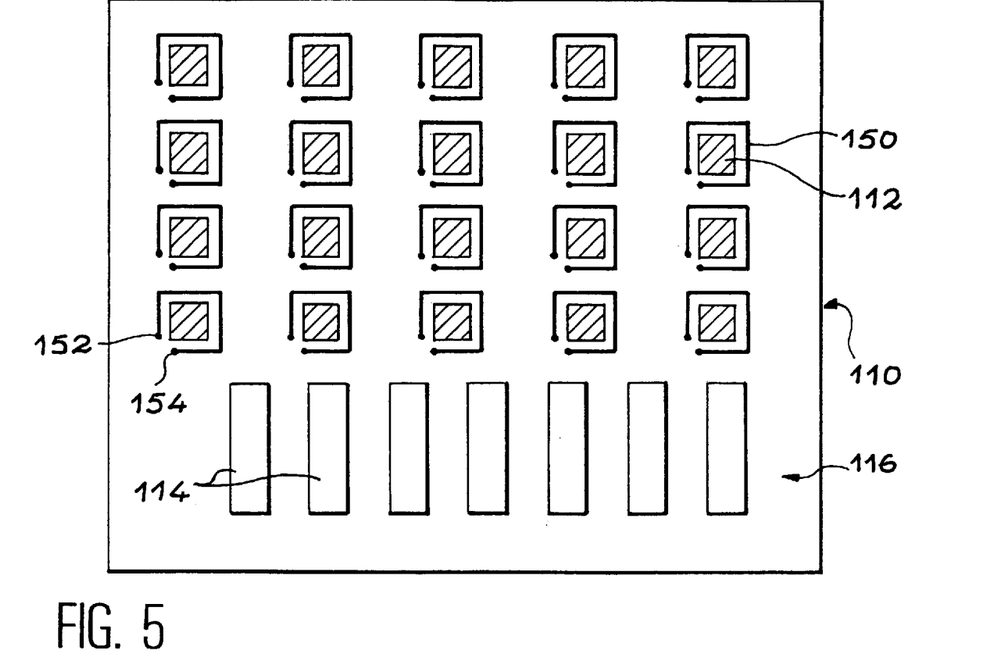
FIG. 5 is a schematic plan view of an electronic chip as used in an analysis device in accordance with the invention.

FIG. 5 shows an electronic chip in accordance with the invention used in an analysis device.

The chip, implemented on a substrate 116, has a plurality of analysis electrodes 112 embodied in the form of metallic blocks, for example blocks of gold or platinum. Each electrode may include one or more mutually isolated metallic blocks.

In FIG. 5, each electrode includes a single metallic block.

The chip also includes, in a peripheral region of the substrate, addressing electrodes 114 capable of being connected to external electrical equipment by means of an appropriate connector, not shown. The external electrical equipment, also not shown, may include current and/or voltage sources to allow electrochemical deposition of reactive materials or probe molecules on the analysis electrodes. The electrical equipment may also include measurement means, for example, for measuring impedances between electrodes.

In order to electrically connect the analysis electrodes and the addressing electrodes, the chip may include, for example, a set of integrated conductive tracks forming connection circuits. The chip may also include multiplexed electronic circuits in order to address a large number of analysis electrodes from a reduced number of addressing electrodes.

It may be noted in FIG. 5 that each analysis electrode 112 is surrounded by a turn in the form of a conductive track 150. The conductive track 150 constitutes a heating resistor which, when it carries a current, makes it possible to raise the temperature of the electrode. It also makes it possible to locally heat an analyte or an electrolyte which might be in contact with the electrode.

Advantageously, a number of addressing electrodes 114 may also be provided for selectively applying to each conductive track 150 a current appropriate to the desired local heating. In this case also, the application of the current to each conductive track may take place through a plurality of independent electrical circuits or through a multiplex type circuit.

These circuits are connected by internal connections, not shown in the figure, to terminals 152 and 154 of each conductive track 150.

The current necessary for the heating may be applied by an appropriate current source external to the chip and connected to the addressing electrodes by a corresponding connector.

According to an advantageous particular aspect, each conductive heating track may also be used as a counter electrode. It is then used at the time of electrochemical treatment for coating the electrodes with a reagent or probe molecules. In this case, the conductive track is also addressable selectively in order to apply thereto an electrical potential appropriate to the electrodeposition.

Figure 6:
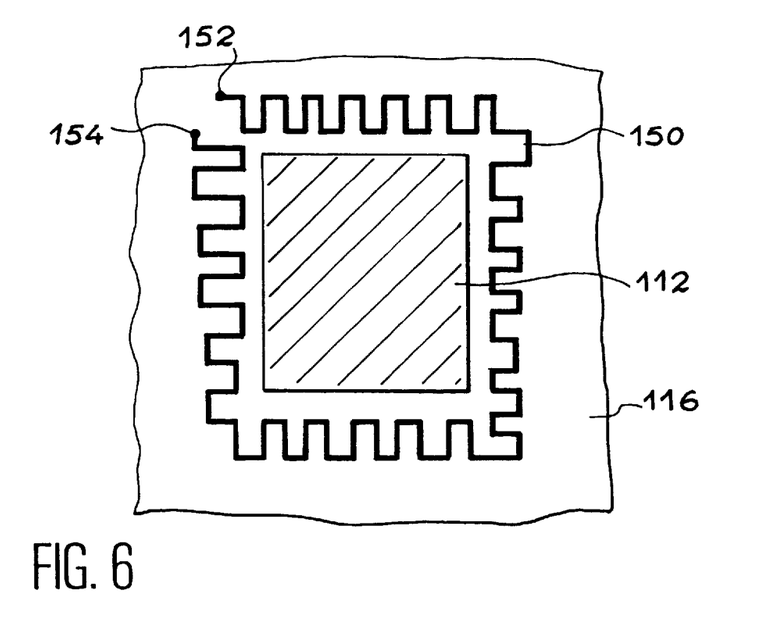
FIG. 6 is an enlarged-scale view illustrating the particular embodiment of an analysis electrode of the electronic chip and of an associated heating track.

FIG. 6 shows, to a larger scale, a particular configuration of an analysis electrode and a conductive heating track associated with it.

Analysis electrode 112, in the form of a square metallic block, is surrounded by a conductive track which has over its path, along the sides of the electrode, a crenellated pattern. This pattern makes it possible to increase the length of conductive track 150 and also to help the heating of the electrode.

As for FIG. 5, references 152 and 154 designate the terminals of conductive track 150.

Figure 7:
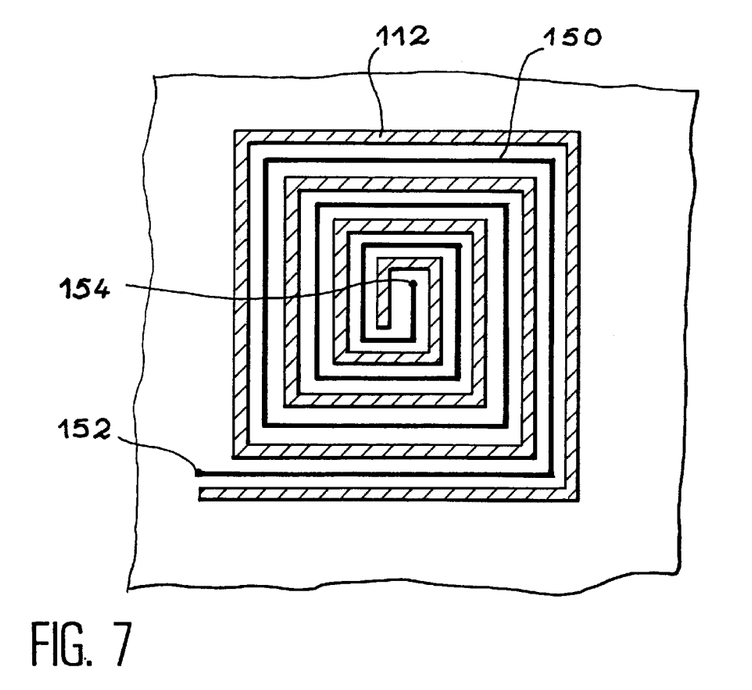
FIG. 7 is an enlarged-scale view illustrating another possible embodiment of an analysis electrode of the electronic chip and of the associated heating track.

Yet another configuration possibility for the electrodes and the conductive heating tracks is depicted in FIG. 7.

According to this configuration, analysis electrode 112 also comes in the form of a conductive track.

The conductive track forming the analysis electrode and the conductive heating track lie substantially parallel and are folded, in this example, into the form of a square spiral.

The terminals of the conductive heating track are indicated with references 152 and 154.

Figure 8:
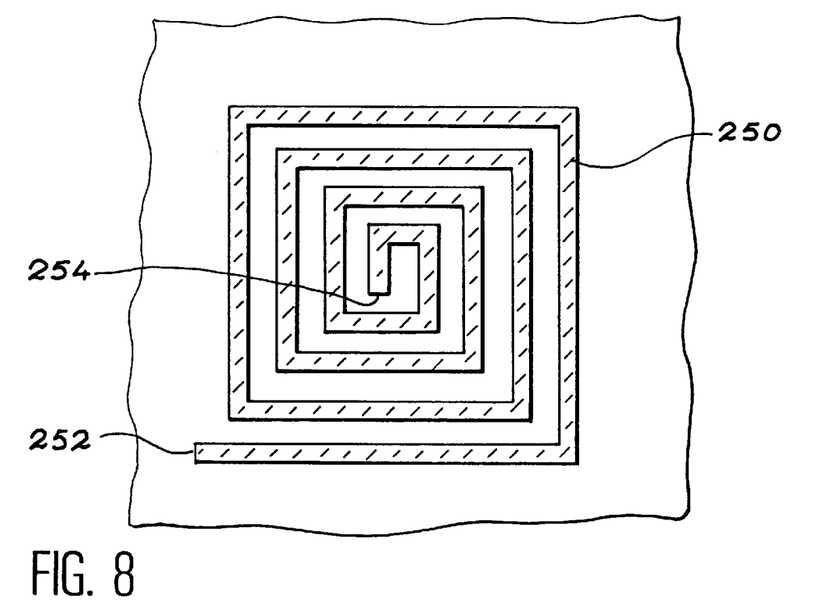
FIG. 8 is an enlarged-scale view illustrating yet another particular embodiment of an analysis electrode of the electronic chip.

FIG. 8 shows yet another embodiment of the electrode and the heating track.

In accordance with this embodiment, a single conductive track 250 forms both the analysis electrode and the means of heating this electrode. Conductive track 250 is folded into the form of a square spiral. End terminals of the track are indicated with references 252 and 254.

Figure 9:
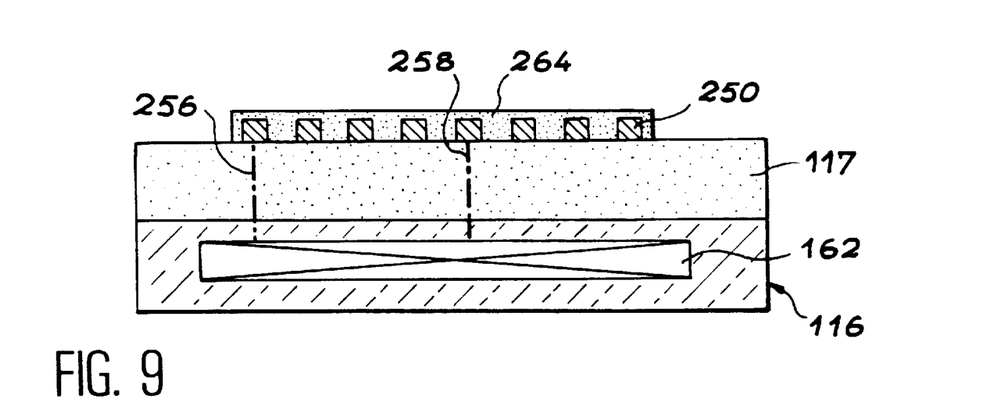
FIG. 9 is a local schematic section of the chip to an enlarged scale, passing through an analysis electrode in accordance with FIG. 8.

FIG. 9 is a local and partial schematic section of a substrate having electrodes in accordance with that shown in FIG. 8.

In FIG. 9, it may be seen that the chip has a surface covered with a layer 117 of an electrically isolating material. It is for example a polyimide layer with a thickness of the order of 15 µm.

Conductive track 250 is formed at the surface of isolating layer 117. Two connection lines indicated very schematically with references 256 and 258 connect respectively terminals 252 and 254 of the conductive track to an addressing device 162 of the chip, also shown very schematically. This addressing device makes it possible, as described above, to selectively apply a heating current to each conductive track, by means of the addressing electrodes.

The material used to form layer 117 is preferentially a polymer material having thermal isolation properties. Thus, the conductive track is isolated thermally, not only from substrate 116 of the chip, but also from the conductive tracks forming the neighbouring conductive electrodes. This thermal isolation makes it possible to make the heating of each individual electrode still more independent.

Furthermore, conductive track 250 may be covered with a thin layer 264 of an electrically isolating material. Thus, a substrate equipped with such electrodes may be used for the analysis of electrically conductive analytes.

In this case however, as track 250 is isolated, the coating with a reagent is not performed by electrochemical means but, for example, with micropipettes.

Figure 10:
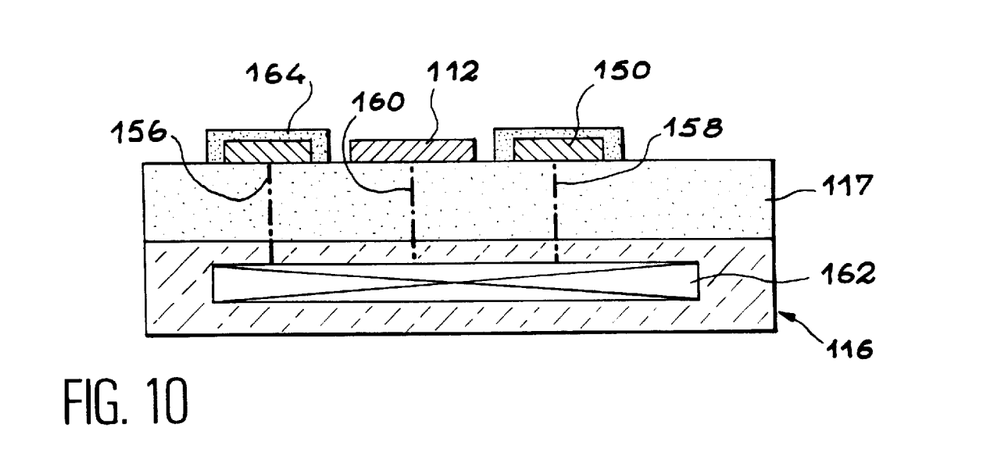
FIG. 10 is a local schematic section of the chip to an enlarged scale, passing through an analysis electrode and a conductive heating track, and illustrating the structure of the chip according to a particular embodiment.
Figure 11:
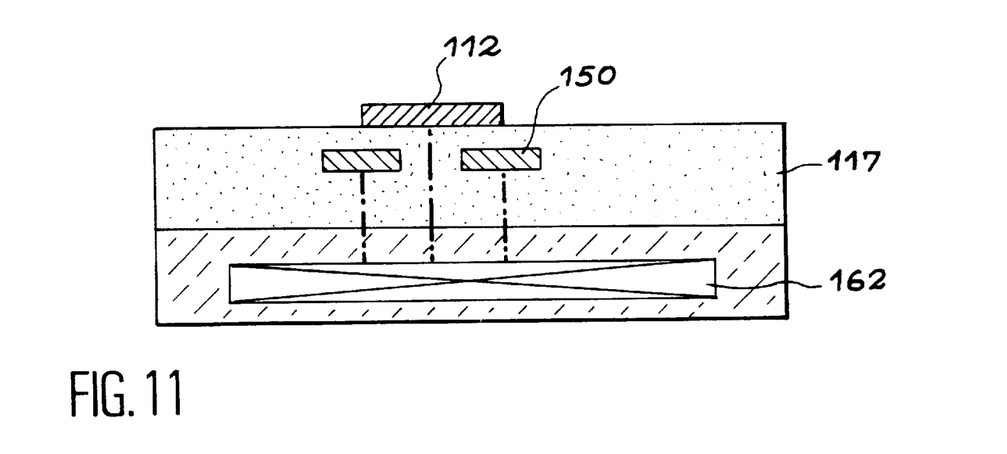
FIG. 11 is a local schematic section of the chip to an enlarged scale, passing through an analysis electrode and a conductive heating track, and illustrating a structure of the chip constituting a variant with respect to the structure of FIG. 10.

FIGS. 10 and 11 also show sections of chips according to other embodiments in which the analysis electrode is distinct from the conductive heating track.

On the chip in FIG. 10, conductive heating track 150 is disposed around analysis electrode 112. It is, just like electrode 112 itself, formed on a layer of electrically isolating material 117 which covers substrate 116 of the chip.

As indicated previously, the electrically isolating material may also be chosen according to its thermal isolation properties. Thus, the conductive heating track, placed in the immediate vicinity of a corresponding electrode, allows the temperature of this electrode to be raised without significantly affecting neighbouring electrodes.

In FIG. 10, references 156, 158 and 160 very schematically indicate electrical connection links connecting respectively the terminals of the conductive heating track and the analysis electrode to addressing circuits 162, also shown schematically.

A thin layer of electrically isolating material 169 may be formed over conductive heating track 150. This layer of electrically isolating material makes it possible to avoid any short circuit or interaction with an analyte brought into contact with the chip. The isolating function of this layer is particularly advantageous when the electrolyte used is highly conductive.

FIG. 11 shows a variant according to which conductive heating track 150, associated with an analysis electrode 112, is buried in the layer of electrically isolating material 117. Conductive heating track 150 is disposed, at least in part, under corresponding electrode 112. It thus occupies less space at the surface of the chip.

As the conductive heating track is buried in the electrically isolating material 117, it is automatically electrically isolated both from analysis electrode 112 and from the analytes with which the chip is liable to be brought into contact.

The conductive heating track is preferably buried at a small distance beneath the surface of the electrically isolating layer, so as to allow sufficient thermal conduction to the analysis electrode.

Figure 12:
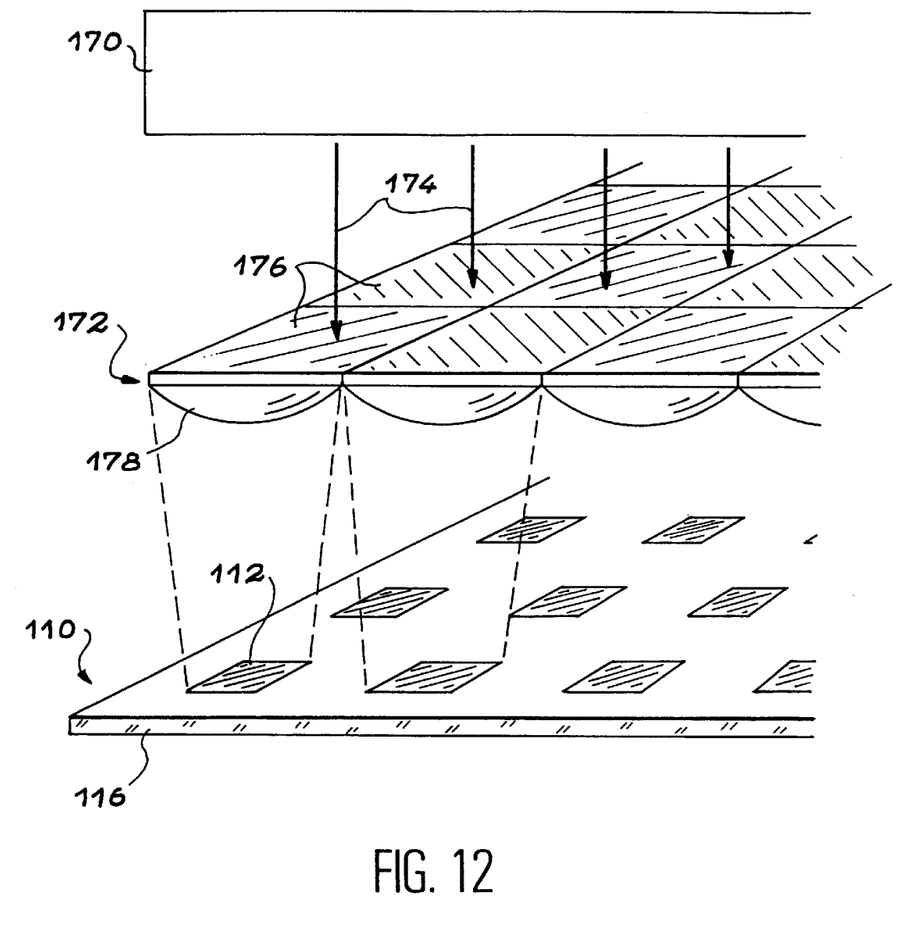
FIG. 12 is a schematic view of a variant of the analysis device in accordance with the invention.

FIG. 12 shows a second embodiment of the invention which does not require any conductive heating tracks or electrical addressing.

Chip 110 used for this embodiment of the invention consists simply of an isolating substrate 116 on which analysis electrodes 112 are formed. Incidentally, the substrate may also have counter electrodes, and addressing electrodes as described previously. It may also be coated with a thermal isolation layer making it possible to reduce the thermal exchanges between the electrodes.

The means of individual heating of analysis electrodes 112 consist of a laser source 170 and a network 172 of microlenses.

Network 172 of microlenses receives a light beam 174 from the laser. It is disposed opposite the analysis electrodes 112 of chip 110 so as to concentrate the light beam 174 selectively on electrodes 112, as indicated in FIG. 12.

The light beam concentrated on the electrodes makes it possible to heat them.

By way of example for a square analysis electrode of side 50 µm, exposed to a laser beam of wavelength 0.5 µm for 1 nsec, it is necessary, in order to obtain at its surface a rise in temperature of 50° C., to apply thereto an instantaneous power of the order of 395 mW.

In a time so short, the depth of penetration of the heat into the electrode is of the order of 10 nm. The heat therefore does not have the time to be removed by the electrode.

The laser source 170 used is, for example, a pulsed microlaser emitting in the green and having a peak power of the order of 200 W to 800 W.

The network of microlenses may have a number of microlenses corresponding to the electrodes to be illuminated and therefore heated.

The network of microlenses may also have a mask with regions 176 of variable density laid out so as to coincide with microlenses 178 of the network.

Thus, the choice of mask and the layout of regions 176, more or less opaque, allows the appropriate selective heating of the corresponding analysis electrodes.

This is because it can be shown that, for microlenses having a dimension of 2d and laid out with a pitch of 2a, the intensity distribution I(x) due to the diffraction of the coherent light from the laser is given by the following formula:

$$I(x)=[f(dx)/dx]^2[\sin(Nax)/Nax]^2,$$

where x represents the angular pitch.

The first term in the above expression represents the envelope. The function f(u) is a sine if the pupil of the microlens is square, and a Bessel function if the pupil is circular.

The second term represents the contribution of N microlenses constituting the network. It should be noted that the intensities of the different light points obtained is not uniform. This is because the microlenses are of large diameter compared with the pitch of the analysis electrodes and with the wavelength of the laser. To that effect the energy distribution of Gaussian light due to the laser is added.

A mask of variable density placed in front of microlenses 178 makes it possible if necessary to correct the non-uniformity of the intensity. It is also possible to not use any mask and to take advantage of the non-uniformity in order to light up and therefore heat differently various analysis electrodes of the chip.

Figure 13:
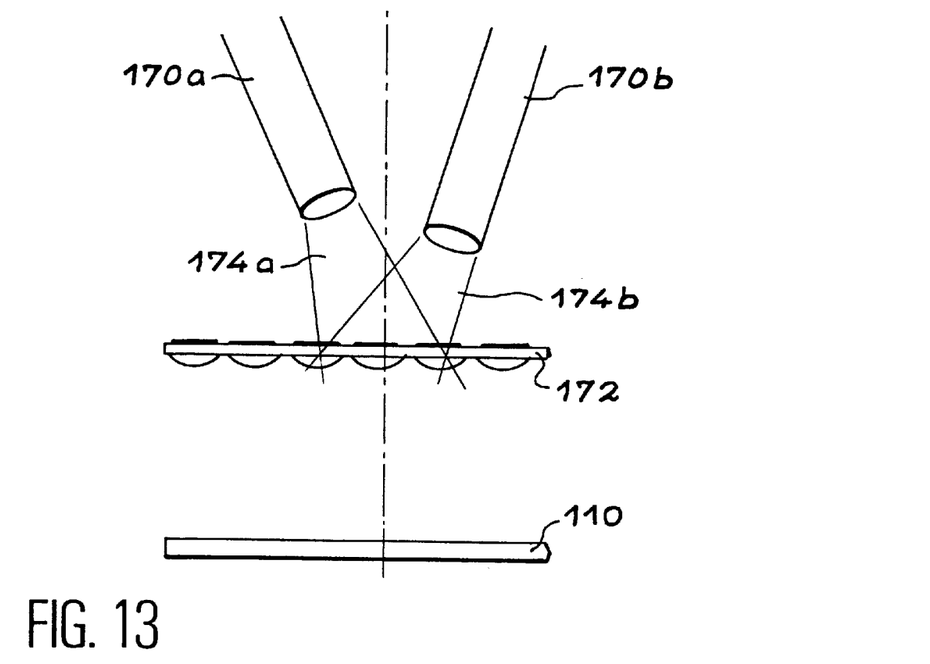
FIGS. 13 and 14 are schematic views illustrating two particular embodiments of the device of FIG. 12.
Figure 14:
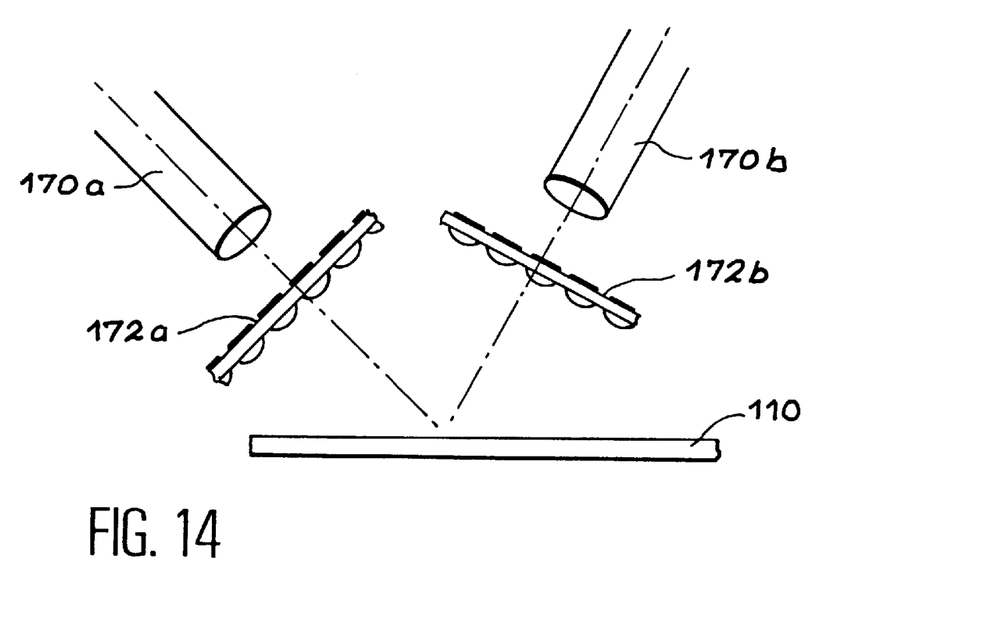

As shown in FIGS. 13 and 14, several laser sources may be used.

In FIG. 13, chip 110 is lit up and heated by two lasers 170a, 170b.

Beams 174a, 174b of lasers 170a and 170b pass through a network 172 of microlenses disposed substantially parallel to the surface of chip 110.

It may be noted that beams 174a and 174b are not perpendicular to network 172 of microlenses and to chip 110. Lasers 170a and 170b are disposed symmetrically with respect to an axis perpendicular to the plane of network 172 of microlenses and to the plane of the surface of chip 110, and form an angle with respect to this axis.

According to a variant, shown schematically in FIG. 14, two distinct networks 172a and 172b of microlenses are used, each network being disposed in front of a laser 170a, 170b.

Each network is disposed substantially perpendicular to the axis of the light beam emitted by the corresponding laser. Furthermore, lasers 170a and 170b are positioned symmetrically so that their beams form an angle with respect to an axis perpendicular to the surface of chip 110.

A suitable combination of one or more lasers and one or more networks of microlenses makes it possible, as indicated previously, to heat differently various analysis electrodes of the chip.

By virtue of this characteristic the chip may be a more ordinary chip not including any conductive heating tracks associated with the electrodes.

The embodiment of the invention in accordance with FIGS. 12 to 14, using heating by means of a laser, may advantageously be combined with an analysis method using fluorescent marking of target molecules. Such a method is described in the introductory part of the text. This is because advantage may be taken of the heating beam to excite the fluorophores of the marked molecules.

What is claimed is:

1. An analysis device including at least one chip (110) equipped with a plurality of analysis electrodes (112), and characterized in that it also includes:

means of individual heating (150, 170) of the analysis electrodes, including, for each analysis electrode, a conductive heating track (150, 250) disposed in the vicinity of the said electrode, the conductive heating track (150) of each analysis electrode forming a counter electrode associated with said analysis electrode; and means of mutual thermal isolation (117) of the analysis electrodes, including a layer (117) of polymer disposed on the chip, the analysis electrodes (112) and the conductive heating tracks (150) being formed on said layer of polymer.

2. An analysis device including at least one chip (110) equipped with a plurality of analysis electrodes (112), and characterized in that it also includes:

means of individual heating (150, 170) of the analysis electrodes, including, for each analysis electrode, a conductive heating track (150, 250) disposed in the vicinity of the said electrode, the conductive heating track (150) of each analysis electrode forming a counter electrode associated with said analysis electrode; and means of mutual thermal isolation (117) of the analysis electrodes comprising a layer (117) of polymer disposed on the chip, the analysis electrodes (112) being formed on said layer of polymer and the conductive heating tracks (150) being buried in the layer of polymer, respectively in the vicinity of the corresponding electrodes.

3. An analysis device including at least one chip (110) equipped with a plurality of analysis electrodes (112), and characterized in that it also includes means of individual heating (150, 170) of the analysis electrodes, said means of individual heating including at least one laser source (170, 170a, 170b) and at least one network of microlenses (172, 172a, 172b) in order to make heating radiation converge towards selected analysis electrodes (112) of said plurality of analysis electrodes.

4. An analysis device according to claim 3, in which the network of microlenses (172) is provide with a mask (176) having regions of variable density and disposed in front of the microlenses.

5. An analysis device including at least one chip (110) equipped with a plurality of analysis electrodes (112), and characterized in that it also includes means of individual heating (150, 170) of the analysis electrodes and means of mutual thermal isolation (117) of the analysis electrodes, said means of mutual thermal isolation of the analysis electrodes including a layer (117) of polymer disposed on the chip, the analysis electrodes (112) and the conductive heating tracks (150) being formed on said polymer layer.

6. An analysis device including at least one chip (110) equipped with a plurality of analysis electrodes (112), and characterized in that it also includes means of individual heating (150, 170) of the analysis electrodes and means of mutual thermal isolation (117) of the analysis electrodes, said means of mutual thermal isolation of the analysis electrodes comprising a layer (117) of polymer disposed on the chip, the analysis electrodes (112) being formed on said layer of polymer and the conductive heating tracks (150) being buried in the layer of polymer, respectively in the vicinity of the corresponding electrodes.

7. An analysis device including at least one chip (110) equipped with a plurality of analysis electrodes (112), and characterized in that it also includes:

means of individual heating (150, 170) of the analysis electrodes, including, for each analysis electrode, a conductive heating track (150, 250) disposed in the vicinity of the said electrode; and means of mutual thermal isolation (117) of the analysis electrodes.

* * * * *